US010117815B2

(12) United States Patent
Jones et al.

(10) Patent No.: US 10,117,815 B2
(45) Date of Patent: Nov. 6, 2018

(54) IMPROVEMENTS RELATING TO ENCAPSULATED BENEFIT AGENTS

(71) Applicant: Conopco, Inc., Englewood Cliffs, NJ (US)

(72) Inventors: Craig Warren Jones, Prenton (GB); Changxi Li, Shanghai (CN); Xiaoyun Pan, Shanghai (CN)

(73) Assignee: CONOPCO, inc., Englewood Cliffs, NJ (US)

( * ) Notice: Subject to any disclaimer, the term of this patent is extended or adjusted under 35 U.S.C. 154(b) by 0 days.

(21) Appl. No.: 14/904,533

(22) PCT Filed: Jul. 28, 2014

(86) PCT No.: PCT/EP2014/066175
§ 371 (c)(1),
(2) Date: Jan. 12, 2016

(87) PCT Pub. No.: WO2015/014792
PCT Pub. Date: Feb. 5, 2015

(65) Prior Publication Data
US 2016/0193125 A1 Jul. 7, 2016

(30) Foreign Application Priority Data

Jul. 30, 2013 (CN) .................. PCT/CN2013/080412
Oct. 17, 2013 (EP) ..................................... 13189102

(51) Int. Cl.
| *A61K 8/31* | (2006.01) |
| *A61Q 19/10* | (2006.01) |
| *A61Q 13/00* | (2006.01) |
| *A61K 8/11* | (2006.01) |
| *B01J 13/14* | (2006.01) |
| *B01J 13/22* | (2006.01) |
| *C09B 67/02* | (2006.01) |
| *C11D 3/50* | (2006.01) |
| *D06M 23/12* | (2006.01) |
| *C11D 17/00* | (2006.01) |
| *C09B 67/08* | (2006.01) |
| *A23L 27/00* | (2016.01) |
| *A61K 8/81* | (2006.01) |
| *A61K 8/88* | (2006.01) |

(52) U.S. Cl.
CPC ................ *A61K 8/31* (2013.01); *A23L 27/72* (2016.08); *A61K 8/11* (2013.01); *A61K 8/8135* (2013.01); *A61K 8/88* (2013.01); *A61Q 19/10* (2013.01); *B01J 13/14* (2013.01); *B01J 13/22* (2013.01); *C09B 67/0013* (2013.01); *C09B 67/0097* (2013.01); *C11D 3/505* (2013.01); *C11D 17/0039* (2013.01); *D06M 23/12* (2013.01); *A61K 2800/412* (2013.01); *A61K 2800/63* (2013.01); *A61K 2800/654* (2013.01); *A61K 2800/95* (2013.01); *A61Q 13/00* (2013.01); *C10N 2250/16* (2013.01)

(58) Field of Classification Search
CPC .......... A61K 8/31; A61K 8/11; A61K 8/8135; A61K 8/88; A61K 2800/654; A61K 2800/95; A61K 2800/412; A61K 2800/63; B01J 13/14; B01J 13/22; C09B 67/0097; C09B 67/0013; C11D 3/505; C11D 17/0039; D06M 23/12; A61Q 19/10; A61Q 13/00; A23L 27/72; C01N 2250/16
See application file for complete search history.

(56) References Cited

U.S. PATENT DOCUMENTS

| 3,870,542 A * | 3/1975 | Ida ........................ B01J 13/025 427/189 |
| 4,145,184 A * | 3/1979 | Brain ...................... C11D 3/505 8/137 |
| 5,460,817 A | 10/1995 | Langley |
| 2004/0071742 A1 | 4/2004 | Popplewell et al. |
| 2004/0072719 A1 | 4/2004 | Bennett et al. |
| 2008/0146478 A1 | 6/2008 | Lei |
| 2010/0073605 A1 * | 3/2010 | Masutani ............. C09K 19/544 349/86 |

(Continued)

FOREIGN PATENT DOCUMENTS

| WO | WO9206672 | 4/1992 |
| WO | WO2009047745 | 4/2009 |
| WO | WO2009103576 | 8/2009 |
| WO | WO2010015493 | 2/2010 |
| WO | WO2011056904 | 5/2011 |
| WO | WO2013026620 | 2/2013 |

OTHER PUBLICATIONS

A new, mild cross-linking methodology to prepare cross-linked enzyme aggregates: retrieved from internet: http://onlinelibrary.wiley.com/doi/10.1002/bit.20033/abstract. Retrieved on Nov. 11, 2016.*

(Continued)

*Primary Examiner* — Hong Yu
(74) *Attorney, Agent, or Firm* — Foley & Lardner LLP

(57) ABSTRACT

A process for the preparation of a particle, wherein the particle comprises: (a) a core comprising a hydrophobic benefit agent; (b) an outer crosslinked shell, which comprises a crosslinked, hydrophobically modified polyvinyl alcohol, which comprises a crosslinking agent comprising a first dextran aldehyde having a molecular weight of from 2,000 to 2,000,000 Da; and (c) an inner polyamide shell, wherein the shell comprises a polyamide, and wherein the polyamide comprises an aromatic group; wherein the outer crosslinked shell is formed prior to the formation of the inner polyamide shell.

12 Claims, No Drawings

(56) References Cited

U.S. PATENT DOCUMENTS

2010/0216684 A1\* 8/2010 Ferguson ........... C11D 17/0039
510/337

OTHER PUBLICATIONS

Chen et al.: Synthesis of poly(diethylenetriamine terephthalamide) and its application as a flame retardant for ABS, retrieved from internet: https://link.springer.com/content/pdf/10.1007%2Fs10973-016-5358-1.pdf. Retrieved on Jul. 6, 2017.\*
Search Report in EP13189102, dated Oct. 6, 2014.
Search Report in PCTEP2014066175, dated Oct. 14, 2014.
Written Opinion in PCTEP2014066175, dated Oct. 14, 2014.
Written Opinionin EP13189102, dated Oct. 6, 2014.

\* cited by examiner

IMPROVEMENTS RELATING TO ENCAPSULATED BENEFIT AGENTS

TECHNICAL FIELD

The present invention is concerned with the delivery of particles comprising benefit agents to substrates, with processes for the manufacture of said particles and the manufacture and use of formulations comprising the same. It will be specifically described herein with reference to laundry treatment compositions but has other and broader applications.

BACKGROUND

Many home care and personal care formulations seek to deliver benefit agents to substrates such as textiles, hard surfaces, hair and skin. Encapsulation of the benefit agent in particles has been proposed as a means of enhancing delivery. Encapsulation of perfumes has generated particular interest and activity in recent years.

Leakage of the benefit agent from the encapsulating particle over time is a known problem with many encapsulates. Leakage into the formulation into which the encapsulate particle has been incorporated leads to instability problems as well as performance issues. Performance issues include not only loss of perfume intensity but also loss of timing of perfume delivery.

Encapsulates comprising polyamides are known in the art.

WO 12/085864 (P&G) Discloses a population of encapsulates, the encapsulates comprising a shell and a core, said shell comprising a polyamide polymer that forms a wall that encapsulates said core, said core comprising a perfume composition. The perfume composition comprises perfume raw materials having a C log P of from 2 to 4.5; the encapsulate has a diameter of from 1 to 100 microns and a fracture strength of from 0.1 to 5 MPa.

U.S. Pat. No. 4,145,184 (P&G) Discloses a laundry detergent composition comprising, a laundry detergent composition comprising: (a) from 2 to 95 percent of a surfactant selected from the group consisting of anionic, nonionic, ampholytic and zwitterionic surfactants, and mixtures thereof; and (b) an effective amount of a perfuming agent comprising a perfume encapsulated in water insoluble, friable microcapsules having an average size of from 5 to 300 microns. The microcapsules have a shell wall material of polyamide.

WO 09/047745 (P&G) Discloses a composition comprising an encapsulate comprising a core comprising a benefit agent and a shell that at least encapsulates said core, said encapsulate further comprising a density balancing agent, said composition being a consumer product. The encapsulate's benefit agent is selected from perfume and shell comprises polyamides.

WO 11/056904 (P&G) Discloses an encapsulate comprising a) a core, comprising perfume and b) shell comprising polyamides.

Melamine formaldehyde capsules are known but, disadvantageously, need to be used in conjunction with a formaldehyde scavenger.

US 2008 146478 (International Flavors and Fragrances Inc) discloses a microcapsule comprising an active material, a nanoscaled material and an encapsulating polymer. The encapsulating polymer is selected from the group consisting of a vinyl polymer, an acrylate polymer, an acrylate acrylamide copolymer, melamine-formaldehyde polymer, urea-formaldehyde polymer and mixtures thereof to form a polymer encapsulated fragrance. See Claims 1, 2 and sections [0111] and [0113]

US 2004 071742 (International Flavors and Fragrances Inc) discloses a composition comprising: a fragrance material; said fragrance material encapsulated by a polymer to provide a polymer encapsulated fragrance; the polymer encapsulated fragrance is further coated by a cationic polymer.

US 2004 072719 (International Flavors and Fragrances Inc) discloses a composition comprising: a fragrance material; said fragrance material encapsulated by a polymer to provide a polymer encapsulated fragrance; the polymer encapsulated fragrance is further coated by a polyamine polymer.

U.S. Pat. No. 5,460,817 (Allied Colloids Ltd) discloses a particulate composition comprising particles having an anhydrous core comprising (a) a solid matrix polymer and an active ingredient distributed throughout the solid matrix polymer and (b) an outer protective coacervated polymer shell. The outer shell is formed of a cross-linked polymer (Polyvinyl alcohol).

WO 92/06672 (Revlon Inc.) Discloses a microencapsulate comprising one or more antiperspirant salts encapsulated within a shell wall which is susceptible to osmotic, enzymatic, or electrolytic degradation, or degradation due to water solubility of the shell wall.

We have now determined that improved particles comprise an outer shell of crosslinked mPVOH, produced with a crosslinking agent comprising a mixture of dextrans having different molecular weights, and an inner shell which comprises a polyamide (which comprises an aromatic group) and a core comprising a perfume. Use of the particles of the invention results in marked improvement in deposition efficiency and a corresponding consumer perceivable increase in benefit delivery.

Advantageously, the new capsules incorporate materials that are made substantially from renewable feedstocks, which helps to reduce environmental impact.

BRIEF DESCRIPTION OF THE INVENTION

Accordingly, in a first aspect the present invention provides a process for the preparation of a particle, wherein the particle comprises:
(a) a core comprising a hydrophobic benefit agent;
(b) an outer crosslinked shell, which comprises a crosslinked, hydrophobically modified polyvinyl alcohol, which comprises a crosslinking agent comprising a first dextran aldehyde having a molecular weight of from 2,000 to 2,000,000 Da; and
(c) an inner polyamide shell, wherein the shell comprises a polyamide, and wherein the polyamide comprises an aromatic group;
wherein the outer crosslinked shell is formed prior to the formation of the inner polyamide shell.

A second aspect of the invention provides a particle obtained from the process of the first aspect, wherein the particle comprises:
(a) a core comprising a hydrophobic benefit agent;
(b) an outer crosslinked shell, which comprises a crosslinked, hydrophobically modified polyvinyl alcohol, which comprises a crosslinking agent comprising a first dextran aldehyde having a molecular weight of from 2,000 to 2,000,000 Da; and (c) an inner polyamide shell, wherein the shell comprises a polyamide, and wherein the polyamide comprises an aromatic group;

wherein the outer crosslinked shell is formed prior to the formation of the inner polyamide shell.

A third aspect provides a liquid composition comprising the particle of the second aspect, which further comprises:—
a) at least one surfactant selected from anionic, cationic, non-ionic and zwitterionic surfactants; and
b) solvent, preferably water.

A fourth aspect of the present invention provides a home care or personal care composition comprising at least one particle according to the second aspect of the invention, the composition preferably being a laundry detergent, laundry conditioner, deodorant, antiperspirant, shampoo, hair conditioner or skin care or skin cleansing product.

A fifth aspect of the present invention provides a method of treatment of a substrate, preferably wherein the substrate is selected from skin, hair and/or textile material, which includes the step of treating the substrate with a composition comprising particles according to the second aspect of the invention.

DETAILED DESCRIPTION OF THE INVENTION

In order that the present invention may be further and better understood it will be further described below with reference to specific embodiments of the invention and further preferred and/or optional features. All amounts quoted are wt % of the total composition unless otherwise stated.

Except in the operating and comparative examples, or where otherwise explicitly indicated, all numbers in this description indicating amounts or ratios of material or conditions of reaction, physical properties of materials and/or use are to be understood as modified by the word "about".

Where a feature is disclosed with respect to a particular aspect of the invention (for example a particle of the invention), such disclosure is also to be considered to apply to any other aspect of the invention (for example a process of the invention) mutatis mutandis.

The Particle

The core is typically formed in an inner region of the particle and provides a sink for the benefit agent. The inner and outer "shells" protect the benefit agent and regulate the flow of benefit agent into and out of the core.

Particle Size

The person of ordinary skill in the art will know how to measure the particle size distribution of the capsules, for example, by utilising a Malvern Mastersizer 2000. Typically, the particle has an average diameter of less than 5-50 micron, preferably from 10 to 40 micron, more preferably from 25 to 35 and most preferably 30 micron.

The Core

The core comprises one or more hydrophobic benefit agent, preferably an organoleptic benefit agent, for example a flavour or fragrance (the terms "fragrance" and "perfume" are used interchangeably herein).

The Benefit Agent

Various benefit agents can be incorporated into the particles. Where the end use of the particles is in connection with a surfactant-containing system, any compatible benefit agent which can provide a benefit to a substrate which is treated with a surfactant composition can be used. Preferred benefit agents are in the laundry field, for example fabric benefit agents, and benefit agents which provide a benefit to a laundry wash and/or rinse medium. In the alternative, benefit agents may provide a skin or hair related benefit. Advantages of the particles of the invention in the presence of surfactant are a good retention of the benefit agent on storage of a formulation and controllable release of the benefit agent during and after product usage.

During the process of the invention, the hydrophobic benefit agent is preferably emulsified by mPVOH. If the benefit agent is solid, it should first be dissolved in oil before use.

Preferred examples include flavours, fragrances, enzymes, antifoams, fluorescers, shading dyes and/or pigments, conditioning agents (for example water-insoluble quaternary ammonium materials and/or silicones), sunscreens, ceramides, antioxidants, reducing agents, sequestrants, colour care additives, density matching polymers, photo-bleaches, lubricants, unsaturated oils, emollients/moisturizers and antimicrobial agents, most preferred are fragrances and antimicrobial agents.

Preferred antimicrobial agents include Triclosan™, climbazole, octapyrox, ketoconizole, zinc pyrithione, and quaternary ammonium compounds.

Preferred sunscreens and/or skin lightening agents are vitamin B3 compounds. Suitable vitamin B3 compounds are selected from niacin, niacinamide, nicotinyl alcohol, or derivatives or salts thereof. Other vitamins which act as skin lightening agents can be advantageously included in the skin lightening composition to provide for additional skin lightening effects. These include vitamin B6, vitamin C, vitamin A or their precursors. Mixtures of the vitamins can also be employed in the composition of the invention. An especially preferred additional vitamin is vitamin B6. Other non-limiting examples of skin lightening agents useful herein include adapalene, aloe extract, ammonium lactate, arbutin, azelaic acid, butyl hydroxy anisole, butyl hydroxy toluene, citrate esters, deoxyarbutin, 1,3 diphenyl propane derivatives, 2, 5 di hydroxyl benzoic acid a nd its derivatives, 2-(4-acetoxyphenyl)-1,3 dithane, 2-(4-Hydroxylphenyl)-1,3 dithane, ellagic acid, gluco pyranosyl-1-ascorbate, gluconic acid, glycolic acid, green tea extract, 4-Hydroxy-5-methyl-3[2H]-furanone, hydroquinone, 4 hydroxyanisole and its derivatives, 4-hydroxy benzoic acid derivatives, hydroxycaprylic acid, inositol ascorbate, kojic acid, lactic acid, lemon extract, linoleic acid, magnesium ascorbyl phosphate, 5-octanoyl salicylic acid, 2,4 resorcinol derivatives, 3,5 resorcinol derivatives, salicylic acid, 3,4,5 trihydroxybenzyl derivatives, and mixtures thereof.

Preferred sunscreens useful in the present invention are 2-ethylhexyl-p-methoxycinnamate, butyl methoxy dibenzoylmethane, 2-hydroxy-4-methoxybenzophenone, octyl dimethyl-p-aminobenzoic acid and mixtures thereof. Particularly preferred sunscreen is chosen from 2-ethyl hexyl-p-methoxycinnamate, 4,-t-butyl-4'-methoxydibenzoylmethane or mixtures thereof. Other conventional sunscreen agents that are suitable for use in the compositions of the invention include 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexyl-salicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonic benzoxazoic acid and mixtures of these compounds.

Preferred anti-oxidants include vitamin E, retinol, anti-oxidants based on hydroxytoluene such as Irganox™ or commercially available antioxidants such as the Trollox™ series.

Perfume and fragrance materials (which include pro-fragrances) are a particularly preferred benefit agent.

The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols. In their natural state, plant lipids comprise antioxidants to prevent their oxidation. While these may be at least in part removed during the isolation of oils from plants some antioxidants may remain. These antioxidants can be pro-fragrances. In particular, the carotenoids and related compounds including vitamin A, retinol, retinal, retinoic acid and provitamin A are capable of being converted into fragrant species including the ionones, damascones and damscenones. Preferred pro-fragrance food lipids include olive oil, palm oil, canola oil, squalene, sunflower seed oil, wheat germ oil, almond oil, coconut oil, grape seed oil, rapeseed oil, castor oil, corn oil, cottonseed oil, safflower oil, groundnut oil, poppy seed oil, palm kernel oil, rice bran oil, sesame oil, soybean oil, pumpkin seed oil, jojoba oil and mustard seed oil. Perfume components which are odiferous materials are described in further detail below.

The perfume is typically present in an amount of from 10-85% by total weight of the particle, preferably from 15 to 75% by total weight of the particle. The perfume suitably has a molecular weight of from 50 to 500 Dalton. Pro-fragrances can be of higher molecular weight, being typically 1-10 kD.

Useful components of the perfume include materials of both natural and synthetic origin. They include single compounds and mixtures. Specific examples of such components may be found in the current literature, e.g., in Fenaroli's Handbook of Flavour Ingredients, 1975, CRC Press; Synthetic Food Adjuncts, 1947 by M. B. Jacobs, edited by Van Nostrand; or Perfume and Flavour Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally perfumed or flavoured, or of modifying the odour and/or taste of said consumer product.

By perfume in this context is not only meant a fully formulated product fragrance, but also selected components of that fragrance, particularly those which are prone to loss, such as the so-called 'top notes'.

Top notes are defined by Poucher (Journal of the Society of Cosmetic Chemists 6(2):80 [1955]). Examples of well known top-notes include citrus oils, linalool, linalyl acetate, lavender, dihydromyrcenol, rose oxide and cis-3-hexanol. Top notes typically comprise 15-25% wt of a perfume composition and in those embodiments of the invention which contain an increased level of top-notes it is envisaged at that least 20% wt would be present within the particle.

Typical perfume components which it is advantageous to employ in the embodiments of the present invention include those with a relatively low boiling point, preferably those with a boiling point of less than 300, preferably 100-250 Celsius.

It is also advantageous to encapsulate perfume components which have a low Log P (i.e. those which will be partitioned into water), preferably with a Log P of less than 3.0. These materials, of relatively low boiling point and relatively low Log P have been called the "delayed blooming" perfume ingredients and include the following materials:

Allyl Caproate, Amyl Acetate, Amyl Propionate, Anisic Aldehyde, Anisole, Benzaldehyde, Benzyl Acetate, Benzyl Acetone, Benzyl Alcohol, Benzyl Formate, Benzyl Iso Valerate, Benzyl Propionate, Beta Gamma Hexenol, Camphor Gum, Laevo-Carvone, d-Carvone, Cinnamic Alcohol, Cinamyl Formate, Cis-Jasmone, cis-3-Hexenyl Acetate, Cuminic Alcohol, Cyclal C, Dimethyl Benzyl Carbinol, Dimethyl Benzyl Carbinol Acetate, Ethyl Acetate, Ethyl Aceto Acetate, Ethyl Amyl Ketone, Ethyl Benzoate, Ethyl Butyrate, Ethyl Hexyl Ketone, Ethyl Phenyl Acetate, Eucalyptol, Eugenol, Fenchyl Acetate, Flor Acetate (tricyclo Decenyl Acetate), Frutene (tricycico Decenyl Propionate), Geraniol, Hexenol, Hexenyl Acetate, Hexyl Acetate, Hexyl Formate, Hydratropic Alcohol, Hydroxycitronellal, Indone, Isoamyl Alcohol, Iso Menthone, Isopulegyl Acetate, Isoquinolone, Ligustral, Linalool, Linalool Oxide, Linalyl Formate, Menthone, Menthyl Acetphenone, Methyl Amyl Ketone, Methyl Anthranilate, Methyl Benzoate, Methyl Benyl Acetate, Methyl Eugenol, Methyl Heptenone, Methyl Heptine Carbonate, Methyl Heptyl Ketone, Methyl Hexyl Ketone, Methyl Phenyl Carbinyl Acetate, Methyl Salicylate, Methyl-N-Methyl Anthranilate, Nerol, Octalactone, Octyl Alcohol, p-Cresol, p-Cresol Methyl Ether, p-Methoxy Acetophenone, p-Methyl Acetophenone, Phenoxy Ethanol, Phenyl Acetaldehyde, Phenyl Ethyl Acetate, Phenyl Ethyl Alcohol, Phenyl Ethyl Dimethyl Carbinol, Prenyl Acetate, Propyl Bornate, Pulegone, Rose Oxide, Safrole, 4-Terpinenol, Alpha-Terpinenol, and/or Viridine It is commonplace for a plurality of perfume components to be present in a formulation. In the encapsulates of the present invention it is envisaged that there may be four or more, preferably five or more, more preferably six or more or even seven or more different perfume components from the list given of delayed blooming perfumes given above present in the particles.

Another group of perfumes with which the present invention can be applied are the so-called 'aromatherapy' materials. These include many components also used in perfumery, including components of essential oils such as Clary Sage, *Eucalyptus*, Geranium, Lavender, Mace Extract, Neroli, Nutmeg, Spearmint, Sweet Violet Leaf and Valerian. By means of the present invention these materials can be transferred to textile articles that will be worn or otherwise come into contact with the human body (such as handkerchiefs and bed linen).

The Inner Shell

The inner shell comprises a polyamide, which comprises an aromatic group.

The polyamide polymer may comprise at least one water miscible monomer and one water immiscible organic monomer.

The water miscible monomer may comprise a material selected from the group consisting of a diamine, a triamine and mixtures thereof. The diamines and triamines themselves may be selected from the group consisting of diethylene triamine, hexamethylene diamine, ethylene diamine and mixtures thereof.

The water immiscible organic monomer may be selected from the group consisting of diacyl chlorides, triacyl chlorides and mixtures thereof. The diacyl chlorides may be selected from the group consisting of sebacoyl dichloride, adipoyl dichloride, and mixtures thereof and said triacyl chlorides may be selected from the group consisting of teraphthaloyl chloride, trimesoyl chloride, acetyl chloride, benzoyl chloride, 1, 3, 5-benzentricarbonyl chloride, and mixtures thereof.

In one embodiment, said polyamide polymer may comprise two or more water miscible monomers.

The Outer Shell

The outer shell comprises a dextran aldehyde (also referred to herein as the "first dextran aldehyde") having a molecular weight of from 2,000 to 2,000,000 Da, preferably from 5,000 to 1,000,000 Da, even more preferably from 10,000 to 500,000 Da, still more preferably from 15,000 to 250,000 Da.

In a preferred embodiment, the outer shell further comprises a second dextran aldehyde having a molecular weight of from greater than 50,000, to 2,000,000 Da, preferably from 75,000 to 1,000,000, even more preferably from 100,000 to 500,000 Da, still more preferably from 150,000 to 300,000, most preferably 200,000 Da. In this embodiment, it is preferred that the first dextran aldehyde has a molecular weight of from 2,000 to 50,000 Da, preferably from 5,000 to 30,000 Da, even more preferably from 10,000 to 25,000 Da, still more preferably from 15,000 to 22,000, most preferably 20,000 Da. In this embodiment, the preferred wt/wt ratio of the second dextran aldehyde to the first dextran aldehyde is suitably in the range of from 0.1 to 10, preferably from 0.5 to 5 and most preferably from 1 to 2.

Dextran is an •-D-1,6-glucose-linked glucan with sidechains 1-3 linked to the backbone units of the dextran. Typically the degree of branching is approximately 5%. The branches are mostly 1 to 2 glucose units long. It is surprising that an alpha 1-6 polysaccharide should show any affinity for both cellulose and polyester.

The dextran aldehyde materials must contain 2 or more aldehyde groups in order to crosslink.

Dextran aldehyde is advantageously used in an amount of from 2.0 to 5.0 wt %, preferably 2.8 to 3.0 wt %; resulting in uniform and regular capsules.

The total amount of dextran aldehyde is preferably from 0.5 to 5.0 wt %, more preferably from 1.0 to 3.5 wt %, most preferably 2.0 to 3.0 wt %, by total weight of the particle.

The mPVOH (Modified Polyvinyl Alcohol)

The amount of mPVOH was found to influence the capsule preparation. Uniform and regular capsules could only be obtained at appropriate mPVOH concentrations.

The preferred concentration of mPVOH for preparation of the capsules of the invention is in the range of from 0.01 to 3 wt %, more preferably from 0.05 to 2 wt %, most preferably from 0.4 to 0.6 wt %, by weight of the mPVOH solution.

Below this amount, the perfume droplet was not fully emulsified. At amounts greater than this, the resultant capsules became aggregated due to higher probability of inter-crosslinking between capsules.

PVOH (parent material), which has a degree of hydrolysis of from 60 to 99%, is first reacted with a derivatising material such as butyraldehyde to give the mPVOH.

The mPVOH comprises an alkyl chain, generally between $C_3$ to $C_{18}$. Hydrocarbyl chain lengths greater than 22 are undesirable as the parent material from which the derivatising group is obtained reacts poorly or not at all with the polymeric backbone.

The hydrocarbyl chain length of the original function on the parent material from which the derivatising group is obtained is preferably from 4 to 22, more preferably from 5 to 20.

In this context, the number of carbons in the hydrocarbyl group includes any carbon within the chain attached to any other functional group within the derivatising material. For instance, butyraldehyde has a hydrocarbyl chain length of 4.

The derivatising material is preferably present in the polymer at a level of from 0.1 to 40% by weight, based on the total weight of the polymer, more preferably 2 to 30%, most preferably 5 to 15%, e. g. 8 to 12%.

Where the polymeric backbone is based on PVOH, the derivatising material is preferably present at a level such that the number ratio of the derivative groups to the free hydroxyl pairs on the backbone is from 1:3 to 1:30, more preferably 1:4 to 1:20, most preferably 1:7 to 1:15, e. g. 1:8 to 1:13.

Polyvinyl alcohol based polymers preferred for use herein have an average molecular weight of from 1,000 to 300,000, preferably from 2,000 to 100,000, most preferably from 2,000 to 75,000. Hydrolysis, or alcoholysis, is defined as the percent completion of the reaction where acetate groups on the resin are substituted with hydroxyl, —OH, groups. A hydrolysis range of from 60-99% of PVOH-based film-forming resin is preferred, while a more preferred range of hydrolysis is from about 88-99%. As used in this application, the term "PVOH" includes polyvinyl acetate compounds with levels of hydrolysis disclosed herein.

Preferred PVOH polymers preferably have an average degree of saponification within the range from 70 to 99%, and a viscosity as a 7% solution within the range 100 to 5000 mPa·s at ambient temperature measured at a shear rate of 20 $s^{-1}$.

All of the above polymers include the aforementioned polymer classes whether as single polymers or as copolymers formed of monomer units or as copolymers formed of monomer units derived from the specified class or as copolymers wherein those monomer units are copolymerised with one or more comonomer units.

A particularly preferred polymer for use in the present invention is represented by the formula:

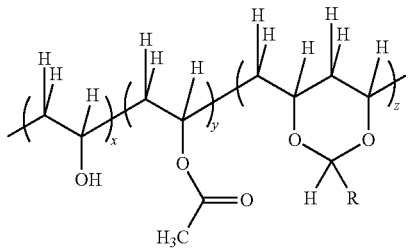

wherein the average number ratio of z to x is within the range of from 1:200 to 1:6, more preferably from 1:100 to 1:8, most preferably from 1:50 to 1:12, e.g. 1:30 to 1:14, y is the residual acetate remaining from the hydrolysis of the parent compound, which is preferably in the range of from 1-20%, more preferably 1-10%, most preferably 1-5% and R is an alkyl or alkenyl group having from 3 to 22 carbon atoms.

More preferably R is an alkyl group having from 3 to 6 carbon atoms. Most preferably R is $C_3H_7$.

Deposition Aids:

The particle optionally comprises a deposition aid. In particularly preferred embodiments the deposition aid is substantive to proteinaceous, cellulosic, polyester, lipid or polyamide surfaces. By use of such a deposition aid, the efficiency of delivery to a specific substrate may be enhanced.

Deposition aids modify the properties of the exterior of the particle. One particular benefit which can be obtained with these materials is to make the particle more substantive to a desired substrate. Desired substrates include cellulosics (including cotton), polyesters (including those employed in the manufacture of polyester fabrics) and protein-containing substrates (such as skin and hair). Deposition aids are preferably selected from non-hydrolysable substrate-substantive polymers, hydrolysable substrate-substantive polymers and polyester-substantive polymers.

Preferred polysaccharide polymers, whether hydrolysable or not may be derived from a broad range of polysaccharides. Preferably, the polysaccharide is selected from the group consisting of: tamarind gum (preferably consisting of xyloglucan polymers), guar gum, locust bean gum (preferably consisting of galactomannan polymers), and other industrial gums and polymers, which include, but are not limited to, Tara, Fenugreek, Aloe, Chia, Flaxseed, *Psyllium* seed, quince seed, xanthan, gellan, welan, rhamsan, dextran, curdlan, pullulan, scleroglucan, schizophyllan, chitin, hydroxyalkyl cellulose, arabinan (preferably from sugar beets), de-branched arabinan (preferably from sugar beets), arabinoxylan (preferably from rye and wheat flour), galactan (preferably from lupin and potatoes), pectic galactan (preferably from potatoes), galactomannan (preferably from carob, and including both low and high viscosities), glucomannan, lichenan (preferably from icelandic moss), mannan (preferably from ivory nuts), pachyman, rhamnogalacturonan, acacia gum, agar, alginates, carrageenan, chitosan, clavan, hyaluronic acid, heparin, inulin, cellodextrins, cellulose, cellulose derivatives and mixtures thereof.

Preferred non-hydrolysable substrate-substantive deposition aids include non-hydrolysable polysaccharides. The polysaccharide preferred for cotton substantivity for example has a β-1,4-linked backbone.

Preferably the polysaccharide is a cellulose, a cellulose derivative, or another β-1,4-linked polysaccharide having an affinity for cellulose, such as polymannan, polyglucan, polyglucomannan, polyxyloglucan and polygalactomannan or a mixture thereof. More preferably, the polysaccharide is selected from the group consisting of polyxyloglucan and polygalactomannan. Most preferably, the deposition aid is locust bean gum, xyloglucan, guar gum or mixtures thereof.

Preferred hydrolysable substrate-substantive deposition aids include hydrolysable polysaccharides. These comprise a polysaccharide which has been modified to render it more water soluble by means of a group covalently attached to the polysaccharide by means of hydrolysable bond. Preferred groups may for example be independently selected from one or more of acetate, propanoate, trifluoroacetate, 2-(2-hydroxy-1-oxopropoxy) propanoate, lactate, glycolate, pyruvate, crotonate, isovalerate cinnamate, formate, salicylate, carbamate, methylcarbamate, benzoate, gluconate, methanesulphonate, toluene, sulphonate, groups and hemiester groups of fumaric, malonic, itaconic, oxalic, maleic, succinic, tartaric, aspartic, glutamic, and malic acids.

Preferred amongst such hydrolysable deposition aids for cotton substantivity is cellulose mono acetate.

Suitable and preferred polyester-substantive deposition aids include phthalate containing polymers, more preferably a polymer having one or more nonionic hydrophilic components comprising oxyethylene, polyoxyethylene, oxypropylene or polyoxypropylene segments, and, one or more hydrophobic components comprising terephthalate segments. Typically, oxyalkylene segments of these deposition aids will have a degree of polymerization of from 1 to about 400, although higher levels can be used, preferably from 100 to about 350, more preferably from 200 to about 300.

One type of preferred deposition aid is a copolymer having random blocks of ethylene terephthalate and polyethylene oxide terephthalate.

Another preferred polymeric deposition aid is polyester with repeat units of ethylene terephthalate units contains 10-15% by weight of ethylene terephthalate units together with 90-80% by weight of polyoxyethylene terephthalate units, derived from a polyethylene glycol of average molecular weight 0.2 kD-40 kD. Examples of this class of polymer include the commercially available material ZELCON 5126 (from DuPont) and MILEASE T (from ICI). Examples of related polymers can be found in U.S. Pat. No. 4,702,857.

Another preferred polymeric deposition aid is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451. Other suitable polymeric soil release agents include the terephthalate polyesters of U.S. Pat. No. 4,711,730, the anionic end-capped oligomeric esters of U.S. Pat. No. 4,721,580, and the block polyester oligomeric compounds of U.S. Pat. No. 4,702,857.

Preferred polymeric deposition aids also include the soil release agents of U.S. Pat. No. 4,877,896 which discloses anionic, especially sulfoarolyl, end-capped terephthalate esters.

Still another preferred deposition aid is an oligomer with repeat units of terephthaloyl units, sulfoisoterephthaloyl units, oxyethyleneoxy and oxy-1,2-propylene units. The repeat units form the backbone of the oligomer and are preferably terminated with modified isethionate end-caps. A particularly preferred deposition aid of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. Said soil release agent also comprises from about 0.5% to about 20%, by weight of the oligomer, of a crystalline-reducing stabilizer, preferably selected from the group consisting of xylene sulfonate, cumene sulfonate, toluene sulfonate, and mixtures thereof.

The deposition aid may be straight or branched. The preferred molecular weight of the polymeric deposition aid is in the range of from about 5 kD to about 500 kD, preferably 10 kD-500 kD, more preferably 20 kD-300 kD.

Preferably, the deposition-aid polymer is present at levels such that the ratio polymer:particle solids is in the range 1:500-3:1, preferably 1:200-1:3.

Preparation Methods:

The benefit agent may be present in the reaction mixture, at a level to give the benefit agent levels in the resulting particles at the levels disclosed above, although it is also possible to form "empty" particles (with or without a benefit agent carrier, for example wax) and subsequently expose them to a benefit agent which can be adsorbed into the inner region.

Deposition aids are generally added to the aqueous phase towards the end of the process, where, for example, further monomer(s) can be added to form further shell material and bind additional materials to the outside of the particle.

Deposition aid may be added at the end of the later phase (preferably after cooling), when for example, further shell forming material (for example an acrylate monomer) are also added to bind the deposition aid to the outer surface of the particle by the formation of further shell material which entraps a portion of the deposition aid and leads to a "hairy" particle in which the "hair" comprises the deposition aid.

For simple core-shell particles, the core excluding benefit agent is less than or equal to 95% wt of mass, and the shell generally 5% wt or greater of the mass of the particle.

Particularly Preferred Embodiments

It is particularly preferred that the above particle comprises a fragrance contained in the core, surrounded by a shell and/or adsorbed into a carrier material, for example a mineral oil, that is surrounded by the shell and/or a polysaccharide deposition aid exterior to the shell. Especially preferred particles have a particle size of 5-50 microns.

Use in Products:

The end-product compositions of the invention may be in any physical form e.g. a solid such as a powder or granules, a tablet, a solid bar, a paste, gel or liquid, especially, an aqueous-based liquid.

The particles of the invention may be advantageously incorporated into surfactant-containing and, in particular laundry and personal care compositions. The particles are typically included in said compositions at levels of from 0.001% to 10%, preferably from 0.005% to 7.55%, most preferably from 0.01% to 5% by weight of the total composition.

For laundry applications, one active ingredient in the compositions is preferably a surface active agent or a fabric conditioning agent.

More than one active ingredient may be included. For some applications a mixture of active ingredients may be used.

Preferably, at least one, for example from 2 to 4, surfactant selected from anionic, cationic, non-ionic and zwitterionic surfactants is present.

Formulated compositions comprising the particles of the invention may contain a surface-active compound (surfactant) which may be chosen from soap and non soap anionic, cationic, non-ionic, amphoteric and zwitterionic surface active compounds and mixtures thereof. Many suitable surface active compounds are available and are fully described in the literature, for example, in "Surface-Active Agents and Detergents", Volumes I and II, by Schwartz, Perry and Berch. The preferred surface-active compounds that can be used are soaps and synthetic non soap anionic, and non-ionic compounds.

The compositions of the invention may contain linear alkylbenzene sulphonate, particularly linear alkylbenzene sulphonates having an alkyl chain length of from C8 to C15. It is preferred if the level of linear alkylbenzene sulphonate is from 0 wt % to 30 wt %, more preferably from 1 wt % to 25 wt %, most preferably from 2 wt % to 15 wt %, by weight of the total composition.

Compositions may contain other anionic surfactants in amounts additional to the percentages quoted above. Suitable anionic surfactants are well-known to those skilled in the art. Examples include primary and secondary alkyl sulphates, particularly C8 to C15 primary alkyl sulphates; alkyl ether sulphates; olefin sulphonates; alkyl xylene sulphonates; dialkyl sulphosuccinates; and fatty acid ester sulphonates. Sodium salts are generally preferred.

Compositions may also contain non-ionic surfactant. Nonionic surfactants that may be used include the primary and secondary alcohol ethoxylates, especially the C8 to C20 aliphatic alcohols ethoxylated with an average of from 1 to 20 moles of ethylene oxide per mole of alcohol, and more especially the 010 to C15 primary and secondary aliphatic alcohols ethoxylated with an average of from 1 to 10 moles of ethylene oxide per mole of alcohol. Non ethoxylated nonionic surfactants include alkylpolyglycosides, glycerol monoethers, and polyhydroxyamides (glucamide).

It is preferred if the level of non-ionic surfactant is from 0 wt % to 30 wt %, preferably from 1 wt % to 25 wt %, most preferably from 2 wt % to 15 wt %, by weight of a fully formulated composition comprising the particles of the invention.

Any conventional fabric conditioning agent may be used. The conditioning agents may be cationic or non-ionic. If the fabric conditioning compound is to be employed in a main wash detergent composition the compound will typically be non-ionic. For use in the rinse phase, typically they will be cationic. They may for example be used in amounts from 0.5% to 35%, preferably from 1% to 30% more preferably from 3% to 25% by weight of a fully formulated composition comprising the particles of the invention.

Suitable cationic fabric softening compounds are substantially water-insoluble quaternary ammonium materials comprising a single alkyl or alkenyl long chain having an average chain length greater than or equal to C20 or, more preferably, compounds comprising a polar head group and two alkyl or alkenyl chains having an average chain length greater than or equal to C14. Preferably the fabric softening compounds have two long chain alkyl or alkenyl chains each having an average chain length greater than or equal to C16. Most preferably at least 50% of the long chain alkyl or alkenyl groups have a chain length of C18 or above. It is preferred if the long chain alkyl or alkenyl groups of the fabric softening compound are predominantly linear.

Quaternary ammonium compounds having two long-chain aliphatic groups, for example, distearyldimethyl ammonium chloride and di(hardened tallow alkyl) dimethyl ammonium chloride, are widely used in commercially available rinse conditioner compositions. Other examples of these cationic compounds are to be found in "Surfactants Science Series" volume 34 ed. Richmond 1990, volume 37 ed. Rubingh 1991 and volume 53 eds. Cross and Singer 1994, Marcel Dekker Inc. New York".

The fabric softening compounds are preferably compounds that provide excellent softening, and are characterised by a chain melting L• to L• transition temperature greater than 25 Celsius, preferably greater than 35 Celsius, most preferably greater than 45 Celsius. This L• to L• transition can be measured by differential scanning calorimetry as defined in "Handbook of Lipid Bilayers", D Marsh, CRC Press, Boca Raton, Fla., 1990 (pages 137 and 337).

Substantially water-insoluble fabric softening compounds are defined as fabric softening compounds having a solubility of less than $1\times10^{-3}$ wt % in demineralised water at 20 Celsius. Preferably the fabric softening compounds have a solubility of less than $1\times10^{-4}$ wt %, more preferably from less than $1\times10^{-8}$ to $1\times10^{-6}$ wt %.

Especially preferred are cationic fabric softening compounds that are water-insoluble quaternary ammonium materials having two C12-22 alkyl or alkenyl groups connected to the molecule via at least one ester link, preferably two ester links. Di(tallowoxyloxyethyl) dimethyl ammonium chloride and/or its hardened tallow analogue is an especially preferred compound of this class.

A second preferred type comprises those derived from triethanolamine (hereinafter referred to as 'TEA quats') as described in for example U.S. Pat. No. 3,915,867. Suitable materials are, for example, N-methyl-N,N,N-triethanolamine ditallowester or di-hardened-tallowester quaternary ammonium chloride or methosulphate. Examples of commercially available TEA quats include Rewoquat WE18 and Rewoquat WE20, both partially unsaturated (ex. WITCO), Tetranyl AOT-1, fully saturated (ex. KAO) and Stepantex VP 85, fully saturated (ex. Stepan).

It is advantageous if the quaternary ammonium material is biologically biodegradable.

It is also possible to include certain mono-alkyl cationic surfactants which can be used in main-wash compositions for fabrics. Cationic surfactants that may be used include quaternary ammonium salts of the general formula R1R2R3R4N+X— wherein the R groups are long or short hydrocarbon chains, typically alkyl, hydroxyalkyl or ethoxylated alkyl groups, and X is a counter-ion (for example, compounds in which R1 is a C8-C22 alkyl group, preferably a C8-C10 or C12-C14 alkyl group, R2 is a methyl group, and R3 and R4, which may be the same or different, are methyl or hydroxyethyl groups); and cationic esters (for example, choline esters).

The choice of surface-active compound (surfactant), and the amount present, will depend on the intended use of the detergent composition. In fabric washing compositions, different surfactant systems may be chosen, as is well known to the skilled formulator, for hand-washing products and for products intended for use in different types of washing machine.

The total amount of surfactant present will also depend on the intended end use and may, in fully formulated products, be as high as 60 wt %, for example, in a composition for washing fabrics by hand. In compositions for machine washing of fabrics, an amount of from 5 to 40 wt % is generally appropriate. Typically compositions will comprise at least 2 wt % surfactant e.g. 2-60%, preferably 15-40% most preferably 25-35%, by weight.

Detergent compositions suitable for use in most automatic fabric washing machines generally contain anionic non-soap surfactant, or non-ionic surfactant, or combinations of the two in any suitable ratio, optionally together with soap.

Compositions, when used as main wash fabric washing compositions, will generally also contain one or more detergency builders. The total amount of detergency builder in compositions will typically range from 5 to 80 wt %, preferably from 10 to 60 wt %, by weight of composition.

Inorganic builders that may be present include sodium carbonate, if desired in combination with a crystallisation seed for calcium carbonate, as disclosed in GB 1 437 950 (Unilever); crystalline and amorphous aluminosilicates, for example, zeolites as disclosed in GB 1 473 201 (Henkel), amorphous aluminosilicates as disclosed in GB 1 473 202 (Henkel) and mixed crystalline/amorphous aluminosilicates as disclosed in GB 1 470 250 (Procter & Gamble); and layered silicates as disclosed in EP 164 514B (Hoechst). Inorganic phosphate builders, for example, sodium orthophosphate, pyrophosphate and tripolyphosphate are also suitable for use with this invention.

The compositions of the invention preferably contain an alkali metal, preferably sodium, aluminosilicate builder. Sodium aluminosilicates may generally be incorporated in end product formulations amounts of from 10 to 70% by weight (anhydrous basis), preferably from 25 to 50 wt %.

The alkali metal aluminosilicate may be either crystalline or amorphous or mixtures thereof, having the general formula: $0.8\text{-}1.5\ Na_2O \cdot Al_2O_3 \cdot 0.8\text{-}6\ SiO_2$.

These materials contain some bound water and are required to have a calcium ion exchange capacity of at least 50 mg CaO/g. The preferred sodium aluminosilicates contain 1.5-3.5 $SiO_2$ units (in the formula above). Both the amorphous and the crystalline materials can be prepared readily by reaction between sodium silicate and sodium aluminate, as amply described in the literature. Suitable crystalline sodium aluminosilicate ion exchange detergency builders are described, for example, in GB 1 429 143 (Procter & Gamble). The preferred sodium aluminosilicates of this type are the well known commercially available zeolites A and X, and mixtures thereof.

The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP 384 070A (Unilever). Zeolite MAP is defined as an alkali metal aluminosilicate of the zeolite P type having a silicon to aluminium weight ratio not exceeding 1.33, preferably within the range of from 0.90 to 1.33, and more preferably within the range of from 0.90 to 1.20.

Especially preferred is zeolite MAP having a silicon to aluminium weight ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono, di¬ and trisuccinates, carboxymethyloxy succinates, carboxymethyloxymalonates, dipicolinates, hydroxyethyliminodiacetates, alkyl and alkenylmalonates and succinates; and sulphonated fatty acid salts. This list is not intended to be exhaustive.

Especially preferred organic builders are citrates, suitably used in fully formulated compositions in amounts of from 5 to 30 wt %, preferably from 10 to 25 wt %; and acrylic polymers, more especially acrylic/maleic copolymers, suitably used in amounts of from 0.5 to 15 wt %, preferably from 1 to 10 wt %.

Builders, both inorganic and organic, are preferably present in alkali metal salt, especially sodium salt, form.

Compositions comprising particles according to the invention may also suitably contain a bleach system. Fabric washing compositions may desirably contain peroxy bleach compounds, for example, inorganic persalts or organic peroxyacids, capable of yielding hydrogen peroxide in aqueous solution.

Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate.

Especially preferred is sodium percarbonate having a protective coating against destabilisation by moisture. Sodium percarbonate having a protective coating comprising sodium metaborate and sodium silicate is disclosed in GB 2 123 044B (Kao).

The peroxy bleach compound is suitably present in a fully formulated product in an amount of from 0.1 to 35 wt %, preferably from 0.5 to 25 wt %. The peroxy bleach compound may be used in conjunction with a bleach activator (bleach precursor) to improve bleaching action at low wash temperatures. The bleach precursor is suitably present in an amount of from 0.1 to 8 wt %, preferably from 0.5 to 5 wt %.

Preferred bleach precursors are peroxycarboxylic acid precursors, more especially peracetic acid precursors and pernoanoic acid precursors. Especially preferred bleach precursors suitable for use in the present invention are N,N,N', N', tetracetyl ethylenediamine (TAED) and sodium nonanoyloxybenzene sulphonate (SNOBS). The novel quaternary ammonium and phosphonium bleach precursors disclosed in U.S. Pat. No. 4,751,015 and U.S. Pat. No. 4,818,426 (Lever Brothers Company) and EP 402 971A (Unilever), and the cationic bleach precursors disclosed in EP 284 292A and EP 303 520A (Kao) are also of interest.

The bleach system can be either supplemented with or replaced by a peroxyacid. Examples of such peracids can be found in U.S. Pat. No. 4,686,063 and U.S. Pat. No. 5,397,501 (Unilever). A preferred example is the imido peroxycarboxylic class of peracids described in EP A 325 288, EP A 349 940, DE 382 3172 and EP 325 289. A particularly preferred example is phthalimido peroxy caproic acid (PAP). Such peracids are suitably present at 0.1-12% wt, preferably 0.5-10% wt.

A bleach stabiliser (transition metal sequestrant) may also be present in fully formulated products. Suitable bleach stabilisers include ethylenediamine tetra-acetate (EDTA), the polyphosphonates such as Dequest (Trade Mark) and non phosphate stabilisers such as EDDS (ethylene diamine di succinic acid). These bleach stabilisers are also useful for stain removal especially in end-products containing low levels of bleaching species or no bleaching species.

An especially preferred bleach system comprises a peroxy bleach compound (preferably sodium percarbonate optionally together with a bleach activator), and a transition metal bleach catalyst as described and claimed in EP 458 397A, EP 458 398A and EP 509 787A (Unilever).

Advantageously in the compositions of the invention benefit agents, particularly, perfume components may be employed which are sensitive to bleaches as the encapsulation of, for example, the perfume component within the particles will provide some degree of protection to the perfume component or other benefit agent.

The fully formulated compositions may also contain one or more enzyme(s).

Suitable enzymes include the proteases, amylases, cellulases, oxidases, peroxidases and lipases usable for incorporation in detergent compositions. Preferred proteolytic enzymes (proteases) are catalytically active protein materials which degrade or alter protein types of stains when present as in fabric stains in a hydrolysis reaction. They may be of any suitable origin, such as vegetable, animal, bacterial or yeast origin.

Proteolytic enzymes or proteases of various qualities and origins and having activity in various pH ranges of from 4-12 are available and can be used in the instant invention. Examples of suitable proteolytic enzymes are the subtilisins which are obtained from particular strains of *B. Subtilis B. licheniformis*, such as the commercially available subtilisins Maxatase (Trade Mark), as supplied by Genencor International N.V., Delft, Holland, and Alcalase (Trade Mark), as supplied by Novozymes Industri A/S, Copenhagen, Denmark.

Particularly suitable is a protease obtained from a strain of *Bacillus* having maximum activity throughout the pH range of 8-12, being commercially available, e.g. from Novozymes Industri A/S under the registered trade names Esperase (Trade Mark) and Savinase (Trade Mark). The preparation of these and analogous enzymes is described in GB 1 243 785. Other commercial proteases are Kazusase (Trade Mark obtainable from Showa Denko of Japan), Optimase (Trade Mark from Miles Kali Chemie, Hannover, West Germany), and Superase (Trade Mark obtainable from Pfizer of U.S.A.).

Detergency enzymes are commonly employed in fully formulated products in granular form in amounts of from about 0.1 to about 3.0 wt % on product. However, any suitable physical form of enzyme may be used. Advantageously in the compositions of the invention benefit agents, for example, perfume components, may be employed which are sensitive to enzymes as the encapsulation of the perfume component (or other benefit agent) within the particles will provide some degree of protection to the perfume component (or other benefit agent).

The compositions of the invention may contain alkali metal, preferably sodium carbonate, in order to increase detergency and ease processing. Sodium carbonate may suitably be present in fully formulated products in amounts ranging from 1 to 60 wt %, preferably from 2 to 40 wt %. However, compositions containing little or no sodium carbonate are also within the scope of the invention.

The fully formulated detergent composition when diluted in the wash liquor (during a typical wash cycle) will typically give a pH of the wash liquor from 7 to 10.5 for a main wash detergent.

Particulate detergent compositions are suitably prepared by spray drying a slurry of compatible heat insensitive ingredients, and then spraying on or post-dosing those ingredients unsuitable for processing via the slurry. The skilled detergent formulator will have no difficulty in deciding which ingredients should be included in the slurry and which should not. It is particularly useful to add the perfume particles of the present invention via post-dosing.

Particulate detergent compositions preferably have a bulk density of at least 400 g/liter, more preferably at least 500 g/liter. Especially preferred compositions have bulk densities of at least 650 g/liter, more preferably at least 700 g/liter.

Such powders may be prepared either by post tower densification of spray dried powder, or by wholly non tower methods such as dry mixing and granulation; in both cases a high-speed mixer/granulator may advantageously be used. Processes using high speed mixer/granulators are disclosed, for example, in EP 340 013A, EP 367 339A, EP 390 251A and EP 420 317A (Unilever).

Liquid detergent compositions can be prepared by admixing the essential and optional ingredients thereof in any desired order to provide compositions containing components in the requisite concentrations. Liquid compositions according to the present invention can also be in compact form which means it will contain a lower level of water compared to a conventional liquid detergent.

In order that the present invention may be still further understood and carried forth into practice it will be further described with reference to the following examples:

EXAMPLES

Materials Used

Raw materials used in the following examples are summarised in Table 1.

TABLE 1

Name, supplier and description of
materials used in these examples.

| Material | Supplier | Description/Function |
|---|---|---|
| Diethylenetriamine (DETA) | Alfa Acesar | Reactive amine to form the polyamide shell. |
| Terephthaloyl chloride | Aldrich | Reactive acid chloride to form the polyamide shell. |
| Modified Polyvinyl Alcohol (mPVOH); Mowiflex, 15 wt % solution. | Synthesis described below | Shell forming material |
| Dextran, MWt 20K | Herochem Reagent Corp | Cross-linking agent |
| Sodium periodate ($NaIO_4$) | Sinopharm Chemical Reagent Corp. | Oxidant for preparing aldehyde-derived dextran |
| PVA (5-88) | Kuraray | Poly(vinylalcohol) Colloid stabilizer |
| Limonene | TCI | Perfume |

Preparation of mPVOH

A 10 wt % solution of PVOH in water was prepared by placing 100 g PVOH (Mowiol 20-98 (trade name), ex Kuraray Specialities) and 900 g demineralised water into a flask and heating to 70° C. To this, 10 ml of hydrochloric acid (36% aqueous solution) was added to catalyse the reaction and then butyraldehyde was added at an amount of 10% based on total weight of polymer. The mixture was then stirred at 70° C. for 5 hours under an inert atmosphere, after which time the heating was stopped and agitation continued for a further 20 hours at room temperature. The reaction mixture was then brought to a pH of 7 using a sodium hydroxide solution.

The resulting solution was precipitated into acetone to yield the acetalised PVOH polymer and washed repeatedly with acetone (500 ml) and then water (50 ml). It was then dried under vacuum at 70° C. overnight to yield a white polymer.

The following capsules were prepared:—
Hybrid Capsule 1—Hybrid polyamide-mPVOH capsule.
Hybrid Capsule 2—Hybrid polyamide-mPVOH capsule, made in accordance with the invention.
Comparative Capsule A—a polyamide perfume capsule
Comparative Capsule B—dextran crosslinked mPVOH capsule The following methods were used to prepare the capsules for use in these examples:—

I) Preparation of Polyamide Perfume Capsule (Comparative Capsule A)

Comparative Capsule A, comprising perfume Limonene was prepared using the following method:—
Step 1:—The following liquids were prepared:—
Liquid A: 2.4 ml perfume (Limonene) and 0.27 g terephthaloyl chloride were mixed until the terephthaloyl chloride dissolved to obtain an oily liquid.
Water solution B: 30 ml deionised water containing 1 wt % PVA (5-88) was prepared and the pH adjusted to desired value using 1M NaOH.
Water solution C: 3.9 ml DETA was dissolved in 6 ml deionised water.
Step 2:—Liquid A was then added to solution B under homogenization at 6000 rpm and the mixture emulsified for 5 min. Solution C was then added dropwise into the emulsion and homogenization was continued for 10 min. The resulting suspension of polyamide capsules, designated "Comparative Capsule A" was allowed to age for 24 h to obtain the capsule slurry for use in the following examples.

II) Preparation of Dextran Crosslinked mPVOH Capsule (Comparative Capsule B)

Preparation of Dextran Crosslinker

An aldehyde-derived dextran was first prepared as follows:—

50 ml of a 4% aqueous solution of sodium periodate ($NaIO_4$) was prepared in a flask. The pH of the solution was adjusted to about 3.5 by adding 0.5 ml 1M HCl and the solution was then protected from the light by covering the flask with aluminum foil. 1.5 g of dextran (MWt 20,000), was added to the flask and allowed to dissolve. The resultant mixture was heated to 40° C. with stirring for 3 h. The mixture was then dialyzed utilizing a dialysis tube with cut-off MWt of 7000 for 48 h. The resultant material was then ready for use as a crosslinker.

Comparative Capsule B, comprising Limonene perfume, was then prepared using the following method:—

- 32 g 0.5% mPVOH solution was mixed with 480 μl of Limonene perfume in a single-neck flask such that a final ratio of perfume to mPVOH of 3:1 was achieved.
- The mixture was then emulsified by homogenisation at 6000 rpm for 5 min. The flask was then placed in a water bath and heated to 50° C. at rate of about 1° C./min with gentle stirring and the mixture kept at 50° C. for 5 min.
- 0.4 ml of dextran crosslinker, as prepared above, (i.e. aldehyde-derived dextran (20 k) solution (CHO concentration was 0.2 mol/L)) was added to the flask and the mixture kept at 50° C. for a further 1.5 h.
- 500 μl of 1M HCl was then added to adjust the pH to 2-3 and the resultant mixture stirred for another 4.5 h at 50° C.
- The flask was then removed and the perfume capsules, designated "Comparative Capsule B", had been formed in the mixture.

III) Preparation of Hybrid Polyamide-mPVOH (Hybrid Capsule 1)

A polyamide perfume capsule, comprising Limonene perfume, was first prepared in the same way as described above for the preparation of Comparative Capsule A.

The following steps were then taken in order to remove any unreacted DETA from the resulting polyamide capsule slurry.

- The slurry was centrifuged for 10 min at 1000 rpm. 28 ml of clear water in the bottom of the tube was then removed using a long needle injector.
- The remaining slurry was diluted to 42 ml with deionised water.
- The above centrifugation and dilution steps were repeated 6 times.
- The pH of the final polyamide slurry was adjusted to 7 using HCl.

The hybrid capsule was then prepared as follows, using the washed polyamide capsule as seed.

- 21 ml of washed polyamide capsule slurry was combined with 32 g 0.5% mPVOH solution in a single-neck flask with stirring.
- The flask was then placed in a water bath and heated to 50° C. at rate of about 1° C./min with gentle stirring and the mixture kept at 50° C. for 5 min.
- 0.4 ml of dextran crosslinker, as prepared above, (i.e. aldehyde-derived dextran (20 k) solution (CHO concentration was 0.2 mol/L)) was added to the flask and the mixture kept at 50° C. for a further 1.5 h.

500 µl of 1M HCl was then added to adjust the pH to 2-3 and the resultant mixture stirred for another 4.5 h at 50° C.

The flask was then removed and the hybrid capsules were found formed in the mixture.

IV) Preparation of Hybrid Polyamide-mPVOH (Hybrid Capsule 2)

1.2 ml perfume (Limonene) and 0.135 g terephthaloyl chloride were mixed until the terephthaloyl chloride dissolved to obtain an oily liquid.

The oily liquid thus obtained was then added to 32 g 0.5% mPVOH solution in a single-neck flask under stirring.

The mixture was then emulsified by homogenisation at 6000 rpm for 2 min.

0.4 ml of dextran crosslinker, as prepared above, (i.e. aldehyde-derived dextran (20 k) solution (CHO concentration was 0.2 mol/L)) was added to the emulsion and the mixture further homogenised at 6000 rpm for 3 min.

The flask was then placed in a water bath and heated to 50° C. at rate of about 1° C./min with gentle stirring.

500 µl of 1M HCl was then added to adjust the pH to 2-3 and the resultant mixture stirred for another 1 h at 50° C.

1.95 ml DETA was dissolved in 3 ml deionised water and added dropwise into the emulsion.

The resulting mixture was stirred for another 2 h at 50° C.

The flask was then removed and the hybrid capsules were found formed in the mixture.

Example 2: Storage Stability of Hybrid Capsule 1 and Hybrid Capsule 2

Hybrid Capsules 1 and 2 were stored at ambient temperature for a period of 1 month.

Capsules were observed under an optical microscope (Hirox KH7700 3D microscope) before and after storage in order to assess levels of breakage and aggregation.

TABLE 1

Capsule appearance before and after storage.

| Capsule | Capsule appearance fresh | Capsule appearance after storage |
| --- | --- | --- |
| 1 | Good, no aggregation | Seriously broken |
| 2 | Good, no aggregation | Intact |

It was found that Hybrid Capsules 2 had superior storage stability compared with Hybrid Capsules 1.

Example 3: Effect of Drying on Hybrid Capsules 2, Comparative Capsule a and Comparative Capsule B Hybrid Capsule 2, Comparative Capsule A and Comparative Capsule B were subjected to a drying process, where one drop of capsule slurry was dripped on glass slide and then natural drying for 20 min at room temperature.

Capsules were observed under an optical microscope (Hirox KH7700 3D microscope) after drying in order to assess the level of breakage induced by the drying process.

TABLE 2

Capsule appearance after drying.

| Capsule | Capsule appearance after drying |
| --- | --- |
| 2 | Intact |
| A | Broken |
| B | Intact |

It will be seen that Hybrid Capsules 2 had good resistance to drying.

Example 4: Evaluation of Perfume Leakage from Hybrid Capsule 2, Comparative Capsule a and Comparative Capsule B The following method was used to evaluate perfume leakage from Hybrid Capsule 2, Comparative Capsule A and Comparative Capsule B:—

Capsules (in an amount containing 15 mg perfume) were added to 2 g of Lux Body Wash, US formulation, commercially available January to February 2011, in a glass vial and the vial sealed. The mixture was then incubated at 37° C. for 10 days before SPME-GC-MS evaluation for perfume leakage.

2 g Body Wash formulation containing 15 mg free perfume was prepared as the calibration standard corresponding to 100% leakage. Likewise, a logarithmic scale of target concentrations as the calibration standards were prepared corresponding to 1.0, 1.8, 3.2, 5.6, 10, 18, 32, 56% leakage.

Calibrations, samples and control were all measured ideally in the same run.

The leakage of perfume capsule in Body Wash formulation was obtained by comparing the corresponding absorption peak with that of Calibrations. The details of SPME-GC-MS method are given below.

SPME-GC-MS Method:—
Equipment: Agilent 6890 GC equipped with Agilent 5975B MS and PAL CTC sampler
Incubation time: 300 s
Incubation temperature: 30° C.
Extraction time: 10 s
Desorption time: 60 s
Oven: 50° C. hold 1 min, 20° C./min to 180° C., 40° C./min to 280° C. and hold for 2 min, 80° C./min to 200° C., 60° C./min to 140° C., 40° C./min to 100° C.,
Run time: 15 min
Inlet: 250° C., splitless
Carrier: He, 1.0 ml/min
Column: DB-5MS, J&W 122-5532
Acquisition mode: SIM, m/z 71, 136, 150

TABLE 3

Perfume leakage from Hybrid Capsule 2, Comparative Capsule A and Comparative Capsule B in Body Wash formulation.

| Capsule | Perfume (Limonene) leakage (%) |
| --- | --- |
| 2 | 82 |
| A | 88 |
| B | 71 |

2 g Body wash formulation containing 15 mg free perfume was prepared as calibration standard corresponding to 100% leakage.

It will be seen that Hybrid Capsules 2 undergo lower leakage than Comparative Capsule A.

Overall, the capsules of the invention display a unique combination of storage stability, robustness to drying and low perfume leakage.

Example 5: Evaluation of Long-Lasting Freshness of Hybrid Capsule 2 and Comparative Free Perfume 1.2 ml perfume limonene and 37.7 ml of 0.01% mPVOH solution were homogenized, and the resulting mixture designated Comparative free perfume.

The following method was used to evaluate long-lasting freshness of Hybrid Capsule 2 and Comparative free perfume:

0.5 ml of Hybrid Capsule 2 (in an amount containing 13 mg perfume) or 0.5 ml of Comparative free perfume (in an amount containing 13 mg perfume) was dropped on a piece (6×6 cm) of knitted polyester fabric sheet. The fabric sheet was hung and natural drying at room temperature for 10 min, 20 min, 30 min, 40 min or 120 min periods. Then the fabric was put into 10 ml acetone and sonifiered for 90 s (circulatory pulse mode including 2 second operating and 5 second suspending). The perfume amount in acetone was then evaluated utilizing GC-FID.

GC-FID Method:
Apparatus: HP 6890 plus+
Oven: initial 40° C., hold 1 min, 10° C./min to 200° C. and hold 2 min
Runtime: 19 min
Inlet: 220° C.
Split ratio: 50:1
Detector: 230° C.
Column: Agilent 19091S-133, HP-INNOWax, Polyethylene Glycol
Carrier: Helium
Flow rate: 1.0 ml/min

TABLE 4

Long-lasting freshness of Hybrid Capsule 2 and Comparative free perfume.

| Drying time (min) | The maintained perfume on substrate after drying | |
|---|---|---|
| | Free perfume | Hybrid capsule 2 |
| 0 | 100% | 100% |
| 10 | 75% | 97% |
| 20 | 74% | 93% |
| 30 | 67% | 91% |
| 40 | 52% | 72% |
| 120 | 25% | 49% |

It can be seen that Hybrid Capsule 2 showed better long-lasting freshness than Comparative free perfume.

The invention claimed is:

1. A process for the preparation of a particle, comprising:
    i.) forming an emulsion comprising
       a) an oil phase comprising a hydrophobic benefit agent and a reactive monomer comprising an aromatic group; and
       b) a water phase comprising a hydrophobically modified polyvinyl alcohol;
    ii.) adding a first dextran aldehyde having a molecular weight of from 10,000 to 25,000 Da such that crosslinking of the hydrophobically modified polyvinyl alcohol occurs to form an outer crosslinked shell; and
    iii.) adding a reactive amine such that the reactive monomer in the oil phase undergoes polymerisation to form an inner polyamide shell;
wherein the particle comprises:
    (a) a core comprising the hydrophobic benefit agent;
    (b) an outer crosslinked shell, which comprises a crosslinked, hydrophobically modified polyvinyl alcohol, which comprises a crosslinking agent comprising the first dextran aldehyde having a molecular weight of from 10,000 to 25,000 Da; and
    (c) an inner polyamide shell, wherein the shell comprises a polyamide, and wherein the polyamide comprises an aromatic group;
wherein the outer crosslinked shell is formed prior to the formation of the inner polyamide shell;
wherein the reactive amine comprises at least one water miscible monomer selected from the group consisting of a diamine, a triamine and mixtures thereof, and the reactive monomer comprising an aromatic group comprises one water immiscible organic monomer selected from the group consisting of diacyl chlorides, triacyl chlorides and mixtures thereof; and
wherein the hydrophobically modified polyvinyl alcohol is represented by the formula:

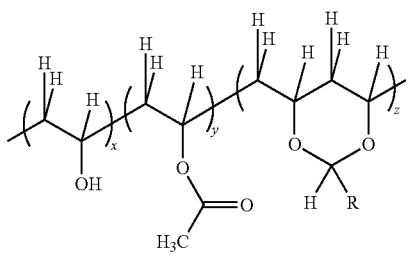

wherein
the average number ratio of z to x is within the range of from about 1:200 to about 1:6;
y is the residual acetate in the range of from about 1 to about 20%, and
R is an alkyl group having from 3 to 6 carbon atoms.

2. A process as claimed in claim 1, wherein the first dextran aldehyde has a molecular weight of from 15,000 to 22,000 Da, and the outer crosslinked shell further comprises a second dextran aldehyde having a molecular weight of from 150,000 to 300,000.

3. A process as claimed in claim 2, wherein the wt/wt ratio of the second dextran aldehyde to the first dextran aldehyde is in the range of from 0.1 to 10.

4. A process as claimed in claim 1, wherein the particle further comprises a deposition aid.

5. A process as claimed in claim 4, wherein the deposition aid is a polysaccharide.

6. A process as claimed in claim 1, wherein the particle has an average diameter of from 5 to 50 microns.

7. A process as claimed in claim 1, wherein the benefit agent is a fragrance, an antimicrobial compound or a mixture thereof.

8. A process as claimed in claim 1, wherein the hydrophobically modified polyvinyl alcohol is modified with butyraldehyde.

9. A process as claimed in claim 8, wherein the core further comprises an additional component selected from a polymeric agent, a solvent and mixtures thereof.

10. A process as claimed in claim 5, wherein the polysaccharide is a non-ionic polysaccharide.

11. A process as claimed in claim 1, wherein the water miscible monomer is selected from the group consisting of diethylene triamine, hexamethylene diamine, ethylene diamine and mixtures thereof.

12. A process as claimed in claim 1, wherein the water immiscible organic monomer is selected from the group consisting of teraphthaloyl chloride, trimesoyl chloride, benzoyl chloride, and mixtures thereof.

* * * * *